United States Patent [19]

Lavanish

[11] 4,233,057
[45] Nov. 11, 1980

[54] 3-[5-(1-PHENOXY-ALKYL, -ALKYNYL, -ALKENYL, OR HALOALKYL)-1,3,4-THIADIAZOL-2-YL]-4-HYDROXY-1-METHYL-2-IMIDAZOLIDINONES

[75] Inventor: Jerome M. Lavanish, Akron, Ohio

[73] Assignee: PPG Industries, Inc., Pittsburgh, Pa.

[21] Appl. No.: 39,021

[22] Filed: May 14, 1979

[51] Int. Cl.³ .................................. C07D 277/38
[52] U.S. Cl. ............................. 71/090; 548/137
[58] Field of Search ..................... 71/88, 90; 548/137

[56] References Cited
U.S. PATENT DOCUMENTS

| | | | |
|---|---|---|---|
| 3,758,492 | 9/1973 | Metzer et al. | 260/306.8 D |
| 3,759,939 | 9/1973 | Metzger et al. | 260/306.8 D |
| 3,849,432 | 11/1974 | Metzger et al. | 260/306.8 D |
| 3,901,904 | 8/1975 | Krenzer | 260/306.8 D |
| 3,901,905 | 8/1975 | Krenzer | 260/306.8 D |
| 3,904,640 | 9/1975 | Krenzer | 260/306.8 D |
| 3,920,674 | 11/1975 | Krenzer | 260/306.8 D |
| 3,925,402 | 12/1975 | Krenzer | 260/306.8 D |
| 3,964,895 | 6/1976 | Krenzer | 260/306.8 D |
| 4,012,223 | 3/1977 | Krenzer | 71/90 |
| 4,023,957 | 5/1977 | Krenzer | 71/90 |
| 4,028,375 | 6/1977 | Krenzer | 260/306.8 D |
| 4,036,848 | 7/1977 | Krenzer | 260/306.8 D |
| 4,052,191 | 10/1977 | Krenzer | 260/306.8 D |
| 4,093,443 | 6/1978 | Krenzer | 260/306.8 D |

Primary Examiner—Nicholas S. Rizzo
Attorney, Agent, or Firm—Robert J. Grassi

[57] ABSTRACT

The disclosed compounds, such as 3-[5-(1-phenoxypropyl)-1,3,4-thiodiazol-2-yl]-4-hydroxy-1-methyl-2-imidazolidinone are useful for controlling weeds postemergence and preemergence.

25 Claims, No Drawings

3-[5-(1-PHENOXY-ALKYL, -ALKYNYL, -ALKENYL, OR HALOALKYL)-1,3,4-THIADIAZOL-2-YL]-4-HYDROXY-1-METHYL-2-IMIDAZOLIDINONES

BACKGROUND OF THE INVENTION

1. Field of the Invention

The invention relates to 5-substituted-(1,3,4-thiadiazol-2-yl)-4-hydroxy-1-methyl-2-imidazolidinones, particularily to the 3-[5-(1-phenoxyalkyl, alkynyl,-alkenyl,-or haloalkyl substituted)-1,3,4-thiadiazol-2-yl]-4-hydroxy-1-methyl-2-imidazolidinone compounds.

2. Description of the Prior Art

Imidazolidinones, as a class, are described in patents and chemical literature, which are silent concerning the novel herbicidal compounds described herein and their use to control the weeds described herein.

SUMMARY OF THE INVENTION

The invention described herein concerns compounds graphically represented by Formula I.

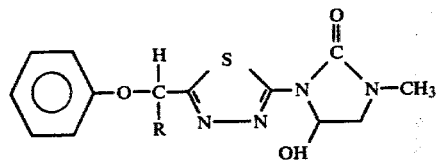

wherein:

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl; the intermediates graphically represented by Formulas III, IV, and V,

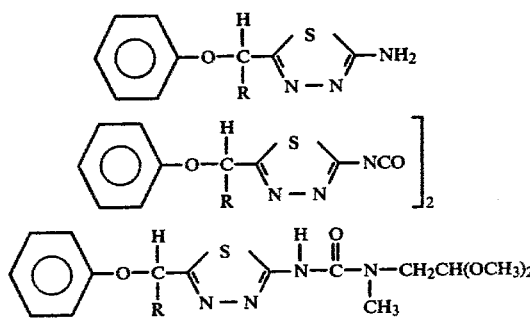

wherein:

R is defined as herein, as well as the process for making compounds of the described formulas. The compounds of Formula I are particularly useful for controlling weeds postemergence and are selective to other weeds both postemergence and preemergence at low rates of applications, particularly compounds wherein R is methyl or ethyl. For example, the compound where R is methyl is useful for controlling wild mustard, morningglory, and barnyardgrass, at preemergence rates of two pounds per acre.

DETAILED DESCRIPTION OF THE INVENTION

The novel agriculturally useful compounds described herein may be graphically represented by Formula I:

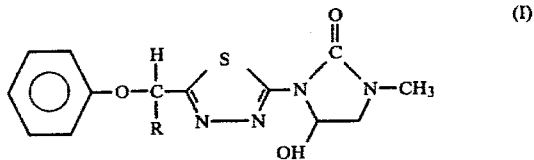

wherein:

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 3-bromoethyl.

Examples of compounds represented by Formula I are:

3-[5-(1-phenoxyethyl)-1,3,4-thiadiazol-2-yl]-4-hydroxy-1-methyl-2-imidazolidinone.

3-[5-(1-phenoxy-2-chloroethyl)-1,3,4-thiadiazol-2-yl]-4-hydroxy-1-methyl-2-imidazolidinone.

3-[5-(1-phenoxy-2-bromoethyl)-1,3,4-thiadiazol-2-yl]-4-hydroxy-1-methyl-2-imidazolidinone.

3-[5-(1-phenoxy-3-chloropropyl)-1,3,4-thiadiazol-2-yl]-4-hydroxy-1-methyl-2-imidazolidinone.

3-[5-(1-phenoxy-3-bromopropyl)-1,3,4-thiadiasol-2-yl]-4-hydroxy-1-methyl-2-imidazolidinone.

3-[5-(1-phenoxy-2-propynyl)-1,3,4-thiadiazol-2-yl]-4-hydroxy-1-methyl-2-imidazolidinone.

3-[5-(1-phenoxy-2-butynyl)-1,3,4-thiadiazol-2-yl]-4-hydroxy-1-methyl-2-imidazolidinone.

3-[5-(1-phenoxy-3-butynyl)-1,3,4-thiadiazol-2-yl]-4-hydroxy-1-methyl-2-imidazolidinone.

3-[5-(1-phenoxy-2-propenyl)-1,3,4-thiadiazol-2-yl]-4-hydroxy-1-methyl-2-imidazolidinone.

3-[5-(1-phenoxy-2-butenyl)-1,3,4-thiadiazol-2-yl]-4-hydroxy-1-methyl-2-imidazolidinone.

3-[5-(1-phenoxy-2-chloroethyl)-1,3,4-thiadiazol-2-yl]-4-hydroxy-1-methyl-2-imidazolidinone.

3-[5-(1-phenoxy-3-butenyl)-1,3,4-thiadiazol-2-yl]-4-hydroxy-1-methyl-2-imidazolidinone.

3-[5-(1-phenoxy-1-pentenyl)-1,3,4-thiadiazol-2-yl]-4-hydroxy-1-methyl-2-imidazolidinone.

3-[5-(1-phenoxy-1-(3-methylbutyl)-1,3,4-thiadiazol-2-yl]-4-hydroxy-1-methyl-2-imidazolidinone.

3-[5-(1-phenoxy-2-(2-methylbutyl)-1,3,4-thiadiazol-2-yl]-4-hydroxy-1-methyl-2-imidazolidinone.

3-[5-(1-phenoxy-1-(2,2-dimethylpropyl)-1,3,4-thiadiazol-2-yl]-4-hydroxy-1-methyl-2-imidazolidinone.

3-[5-(1-phenoxybutyl)-1,3,4-thiadiazol-2-yl]-4-hydroxy-1-methyl-2-imidazolidinone.

3-[5-(1-phenoxy-(2-methylpropyl)-1,3,4-thiadiazol-2-yl]-4-hydroxy-1-methyl-2-imidazolidinone.

3-[5-(1-phenoxypropyl)-1,3,4-thiadiazol-2-yl]-4-hydroxy-1-methyl-2-imidazolidinone.

Although all of the compounds described herein are useful for the purpose described herein, some compounds are more useful than others. Those compounds in which R is an alkynyl, are of a general utility, while those compounds in which R is an alkenyl, are of better utility. Those compounds in which R is a haloalkyl described herein are of high utility and of these, the preferred compounds are those in which R is chloromethyl or bromomethyl. Those compounds in which R is an alkyl described herein, are highly preferred and especially preferred are compounds in which the alkyl is methyl, ethyl, or propyl. The following compounds are the most preferred: 3-[5-(1-phenoxypropyl)-1,3,4-thiadiazol-2-yl]-4-hydroxy-1-methyl-2-imidazolidinone, and 3-[5-(1-phenoxyethyl)-1,3,4-thiadiazol-2-yl]-4-hydroxy-1-methyl-2-imidazolidinone.

SYNTHESIS OF THE COMPOUNDS

The synthesis of the compound proceeds according to the general reactions 1, 2, 3, and 4, shown below:

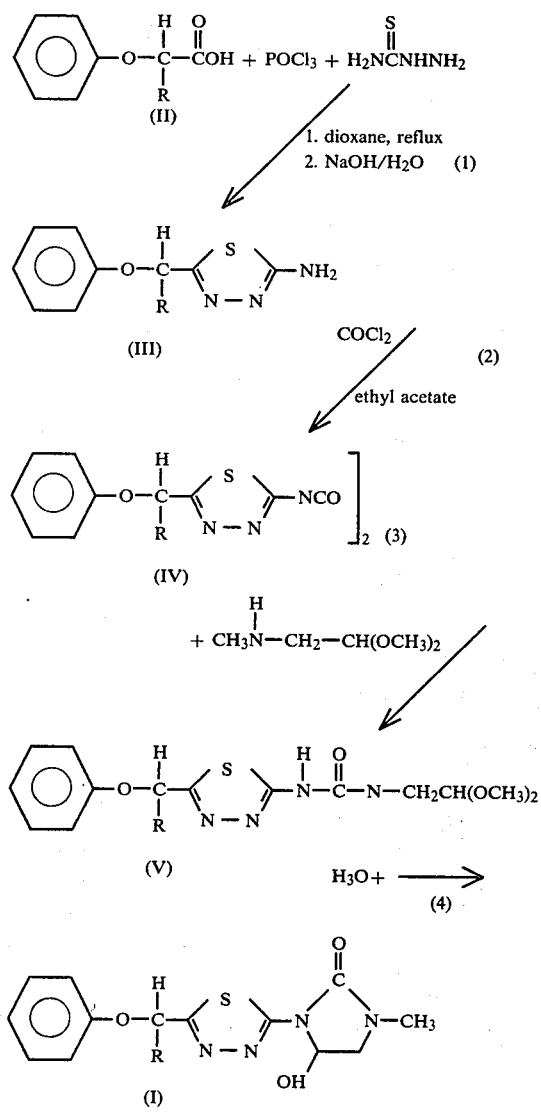

PREPARATION OF 5-SUBSTITUTED 2-AMINO-1,3,4-THIADIAZOLE

The proper alpha substituted carboxylic acid graphically represented by Formula II, wherein R is as described herein (typically 0.4–0.5 moles), an equimolar amount of thiosemicarbazide, and 30-milliliters of dry dioxane, are charged into a hundred milliliter reactor equipped with a thermometer, an efficient stirrer, pressure equilizer, addition funnel, and a condenser-drying tube. The addition funnel is charged with approximately 10 percent excess of phosphorus oxychloride which is added drop wise so as to maintain a reaction temperature of 85°–95° C. and reaction occurs as shown by reaction equation 1. The mixture is then heated to reflux for about 1 hour, after which the solvent is flashed off using a vacuum such as a water aspirator. Water (50 milliliters) is added to the residue to give an emulsion which is then made basic with a 50% sodium hydroxide solution. In those instances that a solid product is obtained (graphically represented by formula III, wherein R is as described herein) the product is isolated by filtration, and recrystalized when necessary. In other cases, the reaction mixture is extracted with ether, the ether layer is separated from the heavier layers, dried over magnesium sulfate, filtered, and concentrated under vacuum to give the crude product represented as a viscous oil.

PREPARATION OF THE ISOCYANATE DIMERS

Five to 10 grams of the appropriate 2-amino-1,3,4-thiadiazole, graphically represented by Formula III, is added to a solution of phosgene in ethylacetate, (or other suitable solvent) prepared by saturating 50-100 milliliters of solvent with phosgene ($COCl_2$) at room temperature then adding another 50–100 milliliters of solvent. The mixture is allowed to stir overnight at room temperature to react as shown by reaction equation 2 and then purged with nitrogen or argon to remove the unreacted phosgene. In those cases where a solid was obtained the product (graphically represented by Formula IV) which is an isocyanate dimer of the appropriate substituted 1,3,4-thiadazole was isolated by filtration and dried. In cases where no solid product is evident, the reaction mixture may be topped under vacuum to give the product as a viscous oil or glass.

PREPARATION OF ACETAL UREAS

The appropriate isocyanate dimer of Formula IV and an equivalent amount of methylamino acetaldehyde dimethylacetal were heated to reflux (5–15 minutes) in an inert solvent such as ether, benzene, or toluene, and the reaction proceeded as shown by reaction equation 3 so as to form the product graphically represented by Formula V. Some products may be produced as crystals directly from solution and others may be induced to crystallize by addition of hexane. The product represented by Formula V may be purified such as by washing with ether, or hexane or recrystalized from hexane/benzene or from ether/benzene, or from ether/chloroform/benzene solutions. Those products or compounds that are represented by Formula V obtained as oils need not be purified.

PREPARATION OF THE COMPOUNDS OF FORMULA I

The appropriate acetal urea of Formula V (approximately three to four grams) is added to 150–200 milliliters of water containing 1.5–2 milliliters of concentrated hydrochloric acid. The mixture is stirred vigorously and heated to reflux, and reaction proceeds as shown by reaction equation 4. The hydrolysis is monitored by thin layer chromatography (alumina-ethylacetate) until complete, and the product, a compound of Formula I, forms. The product, in some cases, may be crystalized directly from the reaction mixture upon cooling. In other cases, the compounds of Formula I are extracted with chloroform and isolated by stripping the solvent under vacuum. Those compounds which solidify upon concentration are further purified. In some cases, the compounds may be used directly as obtained. In other cases, crystallization is induced by seeding an ether solution with a related compound, which may then be further purified.

EXAMPLES

The following examples illustrate the synthesis of the compounds described herein.

EXAMPLE I

SYNTHESIS OF
3-[5-(1-phenoxyethyl)-1,3,4-thiadiazol-2-yl]-4-hydroxy-1-methyl-2-imidazolidinone a. formation of
5-(1-phenoxyethyl)-2-amino-1,3,4-thiadiazole A 1,000 milliliter, 3-neck flask equipped with a Claisen adaptor, paddle stirrer, thermometer, addition funnel and condenser, was charged with 100 grams (0.602 moles) of 2-phenoxypropanoic acid, (54.8 grams, 0.602 mole) of thiosemicarbazide and 300 ml. of dioxane. The slurry was heated to 85° C. and the addition funnel was charged with phosphorous oxychloride ($POCl_3$). The $POCl_3$ was slowly added (for 70 minutes) while maintaining the temperature within 90°–95° C., and then stirred for an additional 20 minutes. It was refluxed for 105 minutes and cooled. The flask was evacuated by using a water aspirator to remove volatiles (HCl, $POCl_3$ and some dioxane), leaving a viscous residue to which 400 ml of water was added and the residue emulsified. A 50 percent solution of NaOH was added until the pH of the solution was 10, and a solid precipitate formed. The solid precipitate was filtered off, washed with water, air dried, then dried in a vacuum oven at 60° C. to a granular grey solid which was recrystallized from $H_2O$/ethanol mixture, filtered and then dried in a vacuum oven at 60° C. to white needles of 5-(1-phenoxyethyl)-2-amino-1,3,4-thiadiazole. (Melting point 157°–167° C.).

b. Formulation of
5-(1-phenoxyethyl)-1,3,4-thiadiazol-2-yl isocyanate dimer

A 200 ml., 3-neck flask equipped with a magnetic stirrer, thermometer, dry ice condenser/drying tube and inlet from a phosgene ($COCl_2$) tank via a calibrated rotometer was charged with 200 ml of ethylacetate which was saturated with phosgene at 20° C. (approximately 2 moles of phosgene). An additional 300 ml. of ethylacetate was added; (124.4 g., 0.566 mole) of 5-(1-phenoxyethyl)-2-amino-1,3,4-thiadiazole, (prepared above) was added at 0° C. and the mixture was then allowed to warm to room temperature. 100 ml. of glyme was added to facilitate stirring. The resulting solution was stirred overnight, with formation of a crystal mass, which was broken up; more ethylacetate was added to form a solution and then the flask was purged with nitrogen until no $COCl_2$ was detected. The cloudy solution was filtered through a Whatman #42 filter paper to yield a pale yellow solution which was topped on a roto-vac to form 143.3 grams of a pale yellow glass of 5-(1-phenoxyethyl)-1,3,4-thiadiazol-2-yl isocyanate dimer.

c. Formation of
3-[5-(1-phenoxyethyl)-1,3,4-thiadiazol-2-yl]-1-methyl-1-(2,2-dimethoxyethyl)urea During a 40 minute period, and at temperatures starting from 25° C. and ending at 47° C., 69.15 grams (0.580 mole) of methylaminoacetaldehyde dimethylacetate was added dropwise to a 300 ml benzene solution containing 143.3 g. (0.580 mole) of the 5-(1-phenoxyethyl)-1,3,4-thiadiazol-2-yl isocyanate isomer (prepared above) and the resulting solution was refluxed for 15 minutes to form a yellow solution. Hexane (1000 ml) was added and the resulting solution was heated on a steam bath, and then seeded with a few crystals of previously purified product. Upon cooling and standing overnight white crystals formed which were filtered, washed with hexane, air dried and then vacuum dried at 50° C. to give 171.4 grams of a powder of 3-[5-(1-phenoxyethyl)-1,3,4-thiadiazol-2-yl]-1-methyl-1-(2,2-dimethoxyethyl) urea. Melting point 117°–121° C.

d. Synthesis of
3-[5-(1-phenoxyethyl)-1,3,4-thiadiazol-2-yl]-1-methyl-4-hydroxy-2-imidazolidinone A solution containing 10 grams of the 3-[5-(1-phenoxyethyl)-1,3,4-thiadiazol-2-yl]-1-methyl-(2,2-dimethoxyethyl)urea (prepared above) 300 ml. of water and 3 ml. of concentrated hydrochloric acid (HCl) was refluxed for 20 minutes, then cooled and the waxy solid which formed was extracted off with chloroform. The chloroform solution was dried over sodium sulfate ($Na_2SO_4$), filtered, and topped in a roto-vac at 70° C. to yield 8.9 g. of a yellow oil. It was seeded with crystals of previously purified product and allowed to crystallize overnight. The partially crystallized oil was added to 30 ml. of benzene and refluxed on a steam bath, cooled, and the crystals removed by suction filter, and then dried in a vacuum oven at 70° C. to yield 6.2 grams of white crystals of 3-[5-(1-phenoxyethyl)-1,3,4-thiadiazol-2-yl]-1-methyl-4-hydroxy-2-imidazolidinone. Melting point is 158°–161° C.

A second batch of crystals was prepared using a solution of 40.0 grams of 3-[5-(1-phenoxyethyl)-1,3,4-thiadiazol-2-yl]-1-methyl-1-(2,2-dimethoxyethyl)urea (prepared above) 1200 ml. of water and 12 ml. of concentrated HCl, which was refluxed for 18 minutes with formation of a solid, which was filtered off, washed with water, dried in a vacuum oven to 33.2 grams of pale yellow crystals (Melting point 148°–157° C.). These were digested in 70 ml. of benzene, cooled, filtered, and dried in a vacuum oven to yield 26.9 grams of white crystals, melting point 157°–161° C., of 3-[5-(1-phenoxyethyl)-1,3,4-thiadiazol-2-yl]-1-methyl-4-hydroxy-2-imidazolidinone. This batch of crystals was combined with the first batch.

A third batch of crystals were prepared following the procedure of batch 2, to give 27.1 grams of white crystals of 3[5-1-phenoxyethyl)-1,3,4-thiadiazol-2-yl]-1-methyl-4-hydroxy-2-imidazolidinone, melting point 158°–162° C.

The three batches of crystals were combined into a single sample of 3-[5-(1-phenoxyethyl)-1,3,4-thiadiazol-2-yl]-1-methyl-4-hydroxy-2-imidazolidinone.

EXAMPLE II

SYNTHESIS OF 3-[5-(1-phenoxypropyl)-1,3,4-thiadiazol-2-yl]-1-methyl-4-hydroxy-2-imidazolidinone a. Preparation of 5-(1-phenoxypropyl)-2-amino-1,3,4-thiadiazole

The procedure of example Ia was followed, using 21.6 g. (0.12 mole) of 2-phenoxybutyric acid, 10.0 g. (0.12 moles) of thiosemicarbazide, and 90 ml. of dioxane, which was heated to 90° C. Then 19.9 gm. (0.13 moles) of phosphorus oxychloride was added dropwise while the temperature was maintained at about 90° C., and the solution was heated to reflux, then topped with a water aspirator vacuum. 100 ml. of water was added. The addition was made basic with 50 percent sodium hydroxide solution and a precipatate formed which was filtered off, partially dried, and then recrystallized from an ethyl alcohol/water/sodium hydroxide mixture. The crystals were removed by filtration and were air dried leaving 12.1 gm. of pale yellow crystals of 5-(1-phenoxypropyl)-2-amino-1,3,4-thiadiazole., which had a melting point of 173°–176° C. A second crop of crystals 2.2 g. were obtained which had a melting point of from 170°–173° C. These were combined into one sample of crystals of 5-(1-phenoxypropyl)-2-amino-1,3,4-thiadiazole.

b. Formation of 5-(1-phenoxypropyl)-1,3,4-thiadiazole-2-yl isocyanate dimer The procedure of Example Ib was followed using 8 g. of the 5-(1-phenoxypropyl)-2-amino-1,3,4-thiadiazole (prepared above) and 100 ml. of ethylacetate saturated with phosgene. Topping and removing of the phosgene resulted in a glassy, orange residue of 5-(1-phenoxypropyl)-1,3,4-thiadiazol-2-yl isocyanate dimer (10.9 grams).

c. Formation of 3-[5-(1-phenoxypropyl)-1,3,4-thiadiazol-2-yl]-1-methyl-1-(2,2-dimethoxyethyl)urea The procedure of Example Ic was followed using 10.9 grams (0.042 moles) of 5-(1-phenoxypropyl)-1,3,4-thiadiazole-2-yl-isocyanate dimer (prepared above) in 50 milliters of benzene, to which was added 5.0 grams (0.042 moles) of methylaminoacetaldehyde dimethyl acetal. The solution was briefly heated to reflux and then hexane was added, but no crystals formed upon cooling. The solution was topped on a roto-vac and the residue was dissolved in ethyl ether, and cooled over dry ice. Crystals formed, which were removed by suction filter and air dried to obtain 5.9 g. of white crystals of 3-[5-(1-phenoxypropyl)-1,3,4-thiadiazol-2-yl]-1-methyl-1-(2,2-dimethoxyethyl)urea, which had a melting point of 84°–85° C.

d. Synthesis of 3-[5-(1-phenoxypropyl)-1,3,4-thiadiazol-2-yl]-1-methyl-4-hydroxy-2-imidazolidinone The procedure of Example Id was followed using 4 grams of 3-[5-(1-phenoxypropyl)-1,3,4,-thiadiazol-2-yl]-1-methyl-1-(2,2-dimethoxyethyl)urea (prepared above) in 200 ml. of water and 2 ml. of concentrated hydrochloric acid. The solution was refluxed for approximately 15 minutes, cooled and extracted with chloroform. The chloroform extract was dried over magnesium sulfate, filtered and topped with a roto-vac at 70° C.; the residue was crystallized from diethyl ether, and the crystals were removed by suction filtration and air dried to give 2.3 grams of white crystals of 3-[5-(1-phenoxypropyl)-1,3,4-thiadiazol-2-yl]-4-hydroxy-1-methyl-2-imidazolidinone having a melting point of 137°–138° C.

INTERMEDIATE COMPOUNDS

Although the other compounds described herein and represented graphically by Formulas III and IV possess no herbicidal properties, and compounds of Formula V possess herbicidal properties, nevertheless, the compounds represented by the Formulas III, IV, and V are very useful because they are intermediates for the synthesis of the novel compounds represented by Formula I.

APPLICATIONS OF THE COMPOSITIONS AGAINST WEEDS

The novel active compounds of Formula I are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area, and the like. Thus while the application of up to only about one or two ounces of active compound per acre may be sufficient for good control of a light infestation of weeds growing under adverse conditions, the application of 2 pounds or 10 pounds or more of an active compound of Formula I per acre may be required for good control of a dense infestation of hardy perennial weeds growing under favorable conditions.

a. EXAMPLES OF WEEDS WHICH MAY BE CONTROLLED BY THE COMPOUNDS DESCRIBED HEREIN

Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. The compositions set forth herein, when applied in a herbicidally effective amount control field pennycress, ryegrass, goosegrass, chickweed, purslane, smartweed, knotweed, wildbuckwheat, kochia, medic, corn cockle, ragweed, sow-thistle, croton, cuphea, dodder, fumitory, groundsel, hempnettle, knawel, spurge, spurry emex, jungle rice, pondweed, dogfennel, carpetweed, bedstraw, ducksalad, naiad, chestgrass, fall panicum, witchgrass, switchgrass, watergrass, teaseed, wild turnip, and sprangletop; biennials such as wild carrot, matricaria, wild barley, campion, chamomile, burdock, mullein, roundleaved mallow, bull thistle, houndstongue, moth mullein, and purple star thistle; or perennials such as white cockle, perennial ryegrass, quackgrass, canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cat-tail, wintercress, horsenettle, nutsedge, milkweed, and sicklepod.

However, important weeds of the genera against which the compounds of the invention are most effective postemergence at ten pounds per acre are: Sida, Datura, Brassica, Setaria, Sorghum, Sesbania, Abutilon, Ipomea, Avena, and Echinochola. Weed species against which the compounds of the invention are most effective (postemergence) are: *Sida spinosa* (L) (teaweed), *Datura stramonium* (jimsonweed), *Brassica kaber* (wild mustard), *Sorghum halepense* (johnsongrass), *Setaria glauca* (yellow foxtail), *Sesbania spp.* (coffeeweed), *Abutilon theophrasti* (velvetleaf), *Ipomea purpurea* (L) Roth (tall morningglory), *Avena fatua* (wild oats), and *Echinochola crusgalli* (barnyardgrass). When applied at very low rates, up to 5 lbs. per acre, the weed species most effected by the preferred compounds where R is methyl or ethyl are: Sesbania Spp. (coffeeweed), *Ipomea purpurea* (L) Roth (tall morningglory) and *Echinochola crusgalli* (L) (barnyardgrass).

Weeds against which the compositions are most effective when applied preemergence are the genera Ipomea and the species *Impomea purpurea* (L) Roth (tall morningglory) and *Brassica kaber* (wild mustard).

b. DESCRIPTION OF THE METHOD OF CONTROLLING WEEDS

As used herein and in the Claims, the method of controlling the weeds comprises contacting the weeds with a herbicidally effective amount of a composition represented by the general formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, with one or more of the compounds represented by the general Formula (I) described herein. The phrase "herbicidally effective amount" refers to that amount required under the environmental conditions in order to effectively control, that is, by which the weeds are injured so as not to be able to recover from the application of the compound, or to be killed by the compound.

c. GENERAL APPLICATION OF THE COMPOUNDS

For practical use of herbicides the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal formulation according to this invention is illustrated by the following example, in which the quantities are in parts by weight.

EXAMPLE III

PREPARATION OF A DUST

Product of Example I—10
Powdered Talc—90

The above ingredients are mixed in a mechanical grinder-blender and are ground until a homogeneous, freeflowing dust of the desired particle size is obtained. This dust is suitable for direct application to the site of the weed infestation.

d. MIXTURES OF COMPOUNDS ALONE OR IN MIXTURES

Although all of the compounds described herein and represented by the general formula described herein are useful as herbicides, some of these are preferred and are better for applications against weeds. In general, all of the compounds described herein may be used either alone or together in mixtures. When used in mixtures the amount or ratio of one compound to another may vary from 0.01 to 100.

e. MANNER OF APPLICATION OF THE COMPOUNDS OF THIS INVENTION

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations will comprise from about 0.05 to about 95 percent by weight of the active compounds of this invention. In a preferred embodiment of this invention, the herbicidal formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. EXAMPLES OF OTHER PESTICIDES AND HERBICIDES FOR COMBINATIONS

The other herbicides, defoliants, desiccants, and plant growth inhibitors, with which the compounds of this invention can be used in the herbicidal formulations to control weeds, can include: chlorophenoxy herbicides; such as 2,4-D,2,4,5-T, MCPA, MCPB, 4-(2,4-DB), 2,4-DEB, 4-CPB, 4-CPA, 5-CPP, 2,4,5-TES, 3,4-DA, silvex, and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, perbulate, vernolate and the like; substituted urea herbicides such as norea, siduron, dichloroal urea, chloroxuron cycluron, fenuron, monuron, monuron TCA, diuron, linuron, monolinuron, neburon, buturon, trimeturon, and the like; symmetrical triazine herbicides such as simazine, cholazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alphachloro-N-isopropyl-acetamide, 2-chloro-N-isopropylacetanilide, 4-(chloroacetyl) morpholine, 1-(chloroacetyl)piperidine, and the like; chlorinated aliphatic acid herbicides such as TCA, dalapon, 2,3-dichloropropionic acid, 2,2,3-TPA, and the like; chlorinated benzoic acid and phenylacetic acid herbicides wuch as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenyl-acetic acid, 2-methoxy-3,5,6-trichlorophenylacetic acid, 2,5-dichloro-3-nitrobenzoic acid, dual, metribuzin and the like; and such compounds as aminotriazole, maleic hydrazode, phenyl mercuric acetate, endothall, biuret, technical chlordane, dimethyl 2,3,5,6-tetrachlorotetraphthalate, diquat, erbon, DNC, DNBP, dichlorobenil, CPA, diphenamid, dipropalin, trifluoralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dine, bromoxynil, cacodylic acid, CMA, CPMF, cypromid, DCB, DCPA, dichlone, diphenatril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, Such herbicides can also be used with the compositions of this invention in the form of their salts, esters, amides, and other derivatives whenever applicable to the particular parent compounds.

The following examples illustrate the method of controlling the weeds described herein. These examples were conducted under standard laboratory conditions, using standard laboratory procedures.

EXAMPLE IV

When the compound of 3-[5-(1-phenoxyethyl)-1,3,4-thiadiazol-2-yl]-4-hydroxy-1-methyl-2-imidazolidinone (Example 1) was applied preemergence at five pounds per acre to the weed species: Sesbania (coffee weed), *Ipomoea purpurea* (L) roth (tall morningglory), and *Echinochola Crusgalli* (L) (barnyardgrass), at the end of twenty-one days all of the weed species were killed.

EXAMPLE V

The compound 3-[5-(1-(1-phenoxypropyl)-1,3,4-thiadiazole-2-yl]-4-hydroxy-1-methyl-2-imidazolidinone (Example 2) was applied postemergence at ten pounds per acre to the weed species *Sida spinosa* (L) (Teaweed), *Datura stramonium* (jimsonweed), *Brassica kaber* (wild mustard), *Sorghum halepense* (johnsongrass), *Gossypium hirsutum* (L) (cotton), *Setaria glauca* (yellow foxtail), Sesbania species (coffeeweed), *Abutilon theophrasti* (velvetleaf), *Ipomea purpurea* (L) Roth (tall morningglory), *Avena fatua* (wild oats), and *Echinochola crusgalli* (barnyardgrass). All of the weed species were either severly injured or killed at the end of twenty-one days.

EXAMPLE VI

The compound 3-[5-phenoxymethyl-1,3,4-thiadiazole-2-yl]-4-hydroxy-1-methyl-2-imidazolidinone, which was prepared in a manner similar to that of the compounds of example I and II, was applied to the same weed species under the same conditions as in example V. All of the weed species were growing.

Furthermore, some of the compounds, particularly, the preferred compounds mentioned herein when applied at very low rates for example below one and two pounds per acre will not effect crops such as soybeans and wheats.

While the invention has been described with reference to the specific details of certain illustrative embodiments it is not intended that it shall be limited thereby accept so far as such details appear in the accompanying claims.

I claim:

1. A compound graphically represented by Formula I

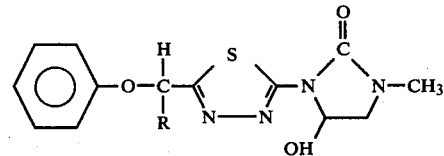

wherein:
R is an alkyl of up to four carbon atoms,
an alkenyl of up to three carbon atoms,
an alkynyl of up to three carbon atoms, or
a haloalkyl selected from the group consisting of chloromethyl, bromomethyl, 2-chloroethyl, and 2-bromoethyl.

2. The compound as recited in claim 1 wherein R is an alkynyl of up to three carbon atoms.

3. The compound as recited in claim 1 wherein R is an alkenyl of up to three carbon atoms.

4. The compound as recited in claim 1 wherein R is a halo alkyl selected from the group consisting of chloromethyl, bromomethyl, 2-chloroethyl, and 2-bromoethyl.

5. The compound as recited in claim 1 wherein R is a haloalkyl selected from the group chloromethyl and bromomethyl.

6. The compound as recited in claim 1 wherein R is an alkyl of up to four carbon atoms.

7. The compound as recited in claim 1 wherein R is an alkyl selected from the group consisting of methyl, ethyl, and propyl.

8. 3-[5-(1-phenoxypropyl)-1,3,4-thiadiazol-2-yl]-4-hydroxy-1-methyl-2-imidazolidinone.

9. 3-[5-(1-phenoxyethyl)-1,3,4-thiadiazol-2-yl]-4-hydroxy-1-methyl-2-imidazolidinone.

10. A method of controlling weeds, which comprises contacting the weeds with a herbicidally effective amount of a compound graphically represented by Formula I

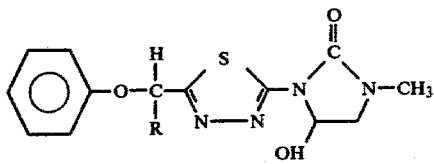

wherein
R is an alkyl of up to four carbon atoms, an alkynyl of up to three carbon atoms, an alkenyl of up to three carbon atoms, or a haloalkyl selected from the group consisting of chloromethyl, bromomethyl, 2-chloroethyl and 2-bromoethyl.

11. The method as recited in claim 10, wherein the weeds are of a genus selected from the group consisting of Sida, Datura, Setaria, Brassica, Sorghum, Sesbania, Abutilon, Ipomoea, Avena, and Echinochola.

12. The method as recited in claim 10, wherein the weeds are of a species selected from the group consisting of Sida spinosa (L), *Datura stramonium* (L), *Setaria glauca* (L), *Brassica kaber* (L), *Sorghum halepense* (L), Sesbania spp., *Abutilon theophrasti* (L), *Ipomoea purpurea* (L), Roth, *Avena fatua* (L), and *Echinochola crusgalli* (L).

13. The method as recited in claim 12 wherein the weeds are contacted postemergence.

14. The method as recited in claim 10 wherein the weeds are growing among crops.

15. The method as recited in claim 11, wherein the weeds are growing among crops.

16. The method as recited in claim 12, wherein the weeds are growing among crops.

17. The method as recited in claim 13, wherein the weeds are growing among crops.

18. The method as recited in any of claims 10, 11, 12, 13, 14, 15, 16, or 17 wherein R is an alkynyl of up to three carbon atoms.

19. The method as recited in any of claims 10, 11, 12, 13, 14, 15, 16, or 17 wherein R is an alkenyl of up to three carbon atoms.

20. The method as recited in any of claims 10, 11, 12, 13, 14, 15, 16, or 17 wherein R is a haloalkyl.

21. The method as recited in any of claims 10, 11, 12, 13, 14, 15, 16, or 17 wherein R is a haloalkyl selected from the group consisting of chloromethyl and bromomethyl.

22. The method as recited in any of claims 10, 11, 12, 13, 14, 15, 16, or 17 wherein R is an alkyl of up to four carbon atoms.

23. The method as recited in any of claims 10, 11, 12, 13, 14, 15, 16, or 17 wherein R is an alkyl selected from the group consisting of methyl, ethyl and propyl.

24. The method as recited in any of claims 10, 11, 12, 13, 14, 15, 16, or 17, wherein the compound is 3-[5-(1-phenoxypropyl)-1,3,4-thiadiazol-2-yl]-4-hydroxy-1-methyl-2-imidazolidinone.

25. The method as recited in any of claims 10, 11, 12, 13, 14, 15, 16, or 17, wherein the compound is 3-[5-(1-phenoxyethyl)-1,3,4-thiadiazol-2-yl]-4-hydroxy-1-methyl-2-imidazolidinone.

* * * * *

UNITED STATES PATENT AND TRADEMARK OFFICE
CERTIFICATE OF CORRECTION

PATENT NO. : 4,233,057
DATED : November 11, 1980
INVENTOR(S) : Jerome M. Lavanish It is certified that error appears in the above—identified patent and that said Letters Patent is hereby corrected as shown below:

On the title page insert

-- [*] Notice: The portion of the term of this patent subsequent to August 9, 1997, has been disclaimed. --

Signed and Sealed this

Twenty-fifth Day of November 1980

[SEAL]

*Attest:*

SIDNEY A. DIAMOND

*Attesting Officer*  *Commissioner of Patents and Trademarks*